United States Patent [19]
Troyer et al.

[11] Patent Number: 5,591,974
[45] Date of Patent: Jan. 7, 1997

[54] AUTOMATED COLLECTION AND PROCESSING OF ENVIRONMENTAL SAMPLES

[75] Inventors: Gary L. Troyer; Susan G. McNeece; Darryl D. Brayton, all of Richland; Amardip K. Panesar, Kennewick, all of Wash.

[73] Assignee: Westinghouse Electric Corporation, Pittsburgh, Pa.

[21] Appl. No.: 954,511

[22] Filed: Sep. 30, 1992

[51] Int. Cl.⁶ ................................................. G01T 7/04
[52] U.S. Cl. ................................. 250/336.1; 250/432 R; 250/435
[58] Field of Search .................................. 250/328, 271, 250/432 R, 435, 304, 370.07, 336.1

[56] References Cited

U.S. PATENT DOCUMENTS

| | | | |
|---|---|---|---|
| 3,348,044 | 10/1967 | Sanders | 250/435 |
| 4,820,925 | 4/1989 | Balmer et al. | 250/379 |
| 5,099,127 | 3/1992 | Kitaguchi et al. | 250/336.1 |
| 5,179,281 | 1/1993 | Tawil et al. | 250/337 |
| 5,468,968 | 11/1993 | Bailey et al. | 250/435 |

FOREIGN PATENT DOCUMENTS

| | | | |
|---|---|---|---|
| 10895 | 1/1984 | Japan | 250/336.1 |
| 2163250 | 2/1986 | United Kingdom | 250/328 |

OTHER PUBLICATIONS

NFSystems Brochure "airQuality System 1", Erwin, Tennessee Jan. 1, 1992.

*Primary Examiner*—Carolyn E. Fields

[57] ABSTRACT

For monitoring an environmental parameter such as the level of nuclear radiation, at distributed sites, bar coded sample collectors are deployed and their codes are read using a portable data entry unit that also records the time of deployment. The time and collector identity are cross referenced in memory in the portable unit. Similarly, when later recovering the collector for testing, the code is again read and the time of collection is stored as indexed to the sample collector, or to a further bar code, for example as provided on a container for the sample. The identity of the operator can also be encoded and stored. After deploying and/or recovering the sample collectors, the data is transmitted to a base processor. The samples are tested, preferably using a test unit coupled to the base processor, and again the time is recorded. The base processor computes the level of radiation at the site during exposure of the sample collector, using the detected radiation level of the sample, the delay between recovery and testing, the duration of exposure and the half life of the isotopes collected. In one embodiment, an identity code and a site code are optically read by an image grabber coupled to the portable data entry unit.

3 Claims, 4 Drawing Sheets

AUTOMATED COLLECTION AND PROCESSING OF ENVIRONMENTAL SAMPLES

The Government has rights in this invention purusant to Contract No. DE-AC06-87RL-10930.

BACKGROUND OF THE INVENTION

1. Field of the Invention

This invention relates to an automated method and apparatus for the collection and processing of environmental samples from a plurality of collection sites. In particular, the invention is a system for monitoring time sensitive environmental parameters at collection sites, such as monitoring radiation levels in a nuclear facility. Distributed sample holders are encoded by optically readable identity labels which are read using a portable scanner or image collection unit upon deployment and collection of the sample holder and upon analysis of the sample. The portable unit automatically indexes the identity code to the time at which the identity code is scanned. The site is also encoded and information respecting certain parameters at the collection site can be encoded and/or compared to stored nominal standards. The data thus collected are downloaded to a processor, for generating an error-free report of the status and trends of the radiation levels at distributed locations, and for monitoring the collection of data in an accountable manner.

2. Prior Art

Certain forms of environmental testing procedures employ sample collectors which are deployed at particular locations to be monitored, and left in place over a period of time. During this time, environmental factors produce changes in the sample collector. By collecting the sample collectors and analyzing their condition it is possible to assess the ambient levels of these environmental factors at the location where the sample collector was deployed. Various environmental factors can be monitored in this way.

One form of relatively demanding environmental monitoring involves testing ambient radiation levels, although the invention is also applicable to monitoring other parameters. It may be desirable to monitor radiation levels in a nuclear power generation plant, in a production or handling facility for nuclear fuel, in weapons facilities, in radiological facilities, etc. It may also be desirable to monitor radiation levels on a more domestic level, for example to detect concentrations of radon.

Ionizing radiation can be sensed using a material which is physically altered by subatomic particles passing through the material, leaving tracks which can be counted. The number of tracks is a function of the radiation level and the time of exposure of the material. Radiation levels can also be detected by accumulating airborne dust in a sample collector, e.g., using a filter and a powered airflow means. The dust can include particles of radioactive isotopes, or for example in the case of radon, the chemical or radioactive decay products which result. These chemical and/or radioactive species are accumulated, trapped or adsorbed, for example being trapped in a filter arrangement coupled to a suction inlet having a known flow rate, or simply deposited on surfaces of material such as charcoal in the sample collector, for quantitative testing.

By detecting radiation emitted from the sample by radioactive decay of isotopes captured by the sample collector, for example by determining the rate of alpha emissions, it is possible to obtain an indirect measure of the concentration of radioactive isotopes at the site of collection. The radioactivity of the material collected is partly a function of the concentration of the radioactive isotope at the testing site and partly a function of the length of time the sample collector was deployed. Similarly, the amount of a chemical species accumulated in this manner can be determined as a measure of the concentration of the chemical species, or of the concentration of a predecessor species in a known reaction.

In measuring concentrations of radioactive materials from radioactive emissions of a collected sample, the half life of radioactive isotopes of interest affects the relationship between the level of radiation during exposure of the sample and the level of radiation emitted by the sample during later testing. The manner in which the sample was collected, such as the extent of air flow through a filter, also affects the amount of material collected. To obtain an accurate measurement for isotopes which have a half life that is relatively short compared to the sampling interval or compared to the delay between recovery of the sample collector and analysis, it may be necessary to compute backwards, with knowledge of the half life of the isotope and the manner of its collection, in order to assess the ambient concentration of the isotope over the period that the sample was taken. It is sometimes necessary to analyze the sample twice, in order to calculate the respective concentrations of isotopes having different half lives, for example testing the sample shortly after recovery of the sample holder, and again after several days.

Typically, samples are collected repeatedly in an ongoing monitoring process. A technician recovers each of the sample collectors, installs a fresh sample collector, and after collecting a group of sample collectors delivers them for testing to analyze their contents. Whereas the accuracy of measurement is critically related to the times of deployment, collection and testing of the sample collector, and in the case of a filter to the volume of air passing through the filter, accuracy of data collection is very important. A large number of sample collectors may be needed to monitor a large number of sites in and around a plant. For these reasons the problem of managing an environmental monitoring system can be formidable.

Sample collectors can be labelled with identity information such as serial numbers or can be kept in packaging materials which are labeled as to collector identity or collection site. At each of the steps (deployment, collection and testing), the time must be recorded and indexed to the particular sample collector. At least once during the process, information identifying the site of deployment must also be recorded to enable the data to be reported as to the specific collection site, and the manner of exposure of the sample collector must be noted. It is then necessary after collecting and analyzing all these data to sort out useful information such as the conditions and trends at the particular sites or at groups of sites having some relationship (e.g., proximity to a potential source of radiation leakage).

It is unavoidable that errors will occur in the collection of all this data. Typically, the name or other identity code of the technician installing, collecting and/or testing the sample is recorded to help track any samples which become lost or otherwise to resolve errors which may occur. This information is also useful for general management information purposes.

Early identification of a problem resulting in an increase in radiation level at a plant site is important to ensure the health of workers, and also to enable a rapid response to equipment failure, should that be the underlying cause of the change in radiation level. It would be desirable to improve the process of data collection in a way that reduces the potential for errors. It would also be desirable to improve data collection in a way that leads smoothly into the process of analyzing the data to identify trends in the data, to cross correlate occurrences on the premises with effects in the detected concentrations, and similarly to accurately gather, and make as much practical use as possible, of the information potentially available.

The present invention ensures accuracy and completeness of data gathering without the need to record sample collector codes, site codes or times manually. This is accomplished by providing a portable apparatus having an on-board processor and optical reader, which automatically stores the time when recording a sample collector code or site code to be referenced to the sample collector. The portable data collector can also input data respecting collection parameters, entered either manually on a keyboard or by automatic means operable to record an optical image of a meter face or the like. The portable data entry unit compares this parameter data with maximum and minimum expected levels of the parameters, stored to define a profile of the respective collection site, enabling corrective action when out-of-range data is presented. The portable apparatus is coupleable in data communication with a computer workstation operable to upload the data from the portable apparatus, and to associate test results from analysis of the contents of the sample collector with the site, the time, and the conditions, and also to monitor the location and chain of custody of sample collectors through the process. In this manner, errors in data collection are substantially reduced and the collected data is available in a manner facilitating automatic processing steps such as statistical and trend analyses, prompt reporting of problems, graphic presentation of the data and management information for improving the efficiency of the process as a whole.

SUMMARY OF THE INVENTION

It is an object of the invention to more accurately and quickly monitor sample collection devices operable to record the effects of environmental variations such as changes in ambient radiation levels.

It is also an object of the invention to keep better track of the location and status of sample collection apparatus associated with time-critical testing processes.

It is another object of the invention to collect data in a sample collection and analysis system that facilitates automated numerical analysis of the results of sample collections.

It is another object of the invention to visually capture meter face or other display readings to minimize human input and reduce the possibility of transcription errors in encoding the values represented by the meter or the like.

These and other objects are accomplished in a method and apparatus for monitoring an environmental parameter, such as the level of nuclear radiation at distributed sites. Automatically readable encoding means are associated with sample collectors which are deployed and their codes are read using a portable data entry unit that also records the time of deployment and collection. The collectors can be filters coupled to inlets of suction means at the sites, and preferably the collectors are encoded by bar code labelling.

The time and collector identity are cross referenced in memory in the portable unit. When later recovering the collector for testing, the code is again read and the time of collection is stored as indexed to the sample collector identity, or to a further bar code, for example as provided on a container for the sample, which is cross referenced to the identity of the sample. At some point in the process, preferably upon deployment, the site of deployment is also entered. For this purpose the respective sites can be identity or location encoded using a bar code label which is scanned or otherwise read. The identity of the operator can also be encoded and stored.

When deploying and/or recovering the sample collectors, the portable data entry unit can accept collection parameter data. For example, the pressure drop across a filter collector or the flow rate in a suction line coupled to the filter can be measured. The portable data collection unit can be programmed to analyze the collection parameter data and to alert the operator if the parameter data is out of a predetermined range stored in memory as a profile indexed to the particular collection site or type of collection site.

The data is transmitted from the portable data unit to a base processor. The samples are tested, preferably using a test unit coupled to the base processor, and again the time is recorded automatically. The base processor associates the deployment, collection and test data for individual samples and computes the level of exposure at the collection site based on the collected data as a whole. For example, the ambient radiation level at the site during exposure of a filter type sample collector can be ascertained from the detected radiation emitted by the collected sample, the delay between recovery and testing, the duration of exposure, the volume of air which passed the filter, and the half life of the isotopes collected. The invention is also applicable to other environmental monitoring situations involving collection of a chemical species for testing, or exposure of a sampling device to the environment at the site for later testing to quantify the effects of such exposure.

Recordation of the data is substantially error proof due to the automated nature of the process. Tracking of the sample collectors and management information is also facilitated. Preferably, the data is used to plot time trends at selected sites and/or spatial distribution of radiation exposure.

The system can support extensive control of the samples and sample collectors, including intermediate identity code reading steps to enable better location monitoring, plural successive testing steps and the like. Alternatively, the invention can be more simply applied as a means to collect accurate data merely as to the duration of exposure and the site at which the sample collector was exposed.

The portable data entry unit used to collect the data is also used to accept an operator identity input. This information together with the location information input from the site code, enable the chain of custody of each sample to be determined later from the data. Thus the present status of each sample can be determined as needed, or the status at a particular time can be checked after the fact. The testing procedures are thus subject to accurate and complete auditing and accountability, as often required for regulatory compliance.

Some variations in the hardware configuration are also possible, including use of portable data entry units which regularly communicate with the base processor by radio, rather than storing data for transfer later. In connection with transfer to the base station, a parking station for a number of portable units can include connectors for coupling the portable units in data communication with the base processor, as well as means for charging batteries in the portable units.

The base processor can generate various reports of radiation levels and temporal or spatial trends, and in general can analyze and report on the samples, the collection sites, the operators and the process in general. A database of information is developed which enables tracking of samples or sample collectors and various forms of statistical analysis.

Preferably, the base processor is coupled to peripheral devices for operator control or data input, display means and printing means for graphic and/or tabular presentation of the data. The printing means is preferably arranged to print bar code labels on appropriate command, for use in labelling collectors or sites. Alternatively, data can be communicated to or from the base processor by associated processors handling one or more of the necessary functions.

The invention is discussed herein with reference to certain embodiments from which an understanding of the invention can be obtained by way of examples. However the invention is not limited only to the examples, and is subject to variations which encompass the novel aspects as defined in the appended claims.

BRIEF DESCRIPTION OF THE DRAWINGS

The invention is discussed with reference to a number of particular examples as shown in the drawings, wherein.

DETAILED DESCRIPTION OF THE PREFERRED EMBODIMENTS

Figure 1:
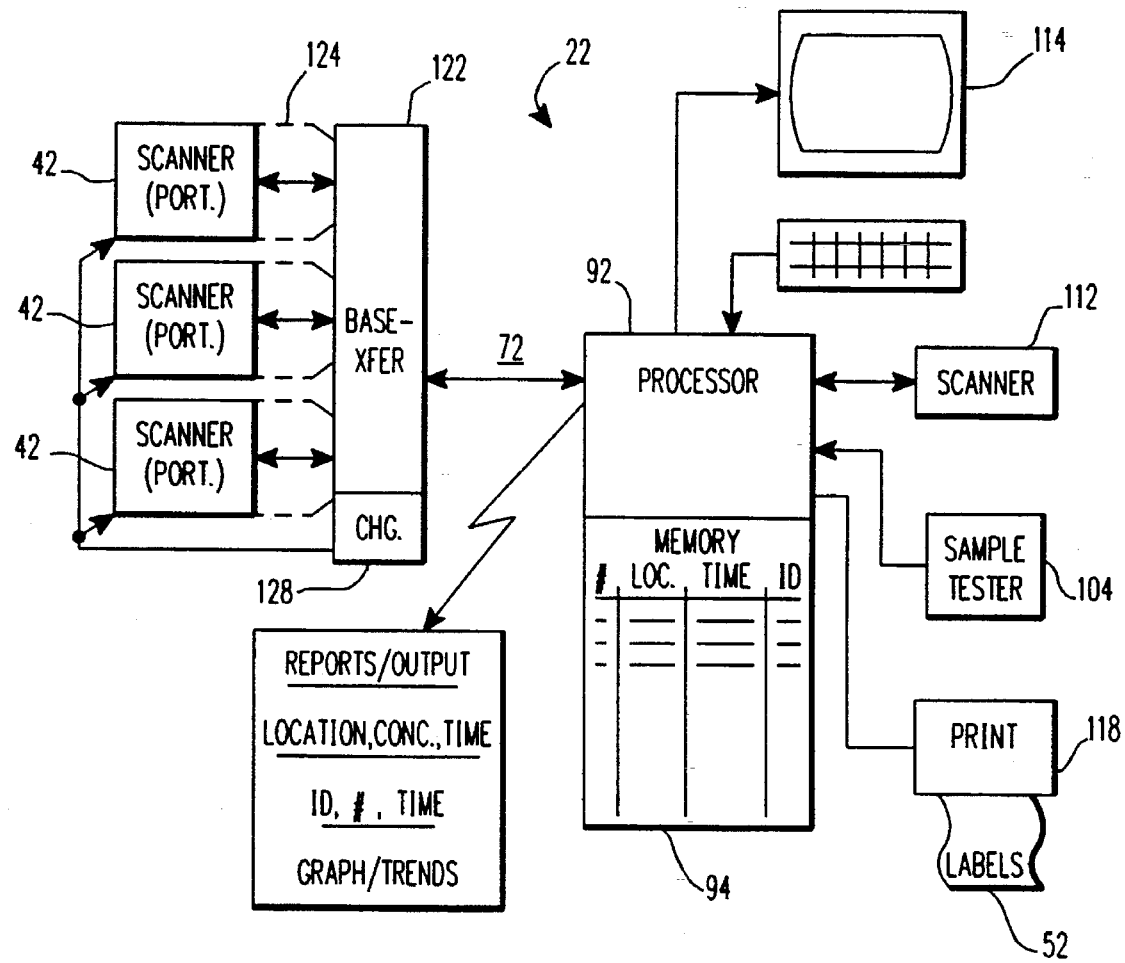
FIG. 1 is a schematic block diagram showing the overall monitoring system according to the invention.
Figure 2:
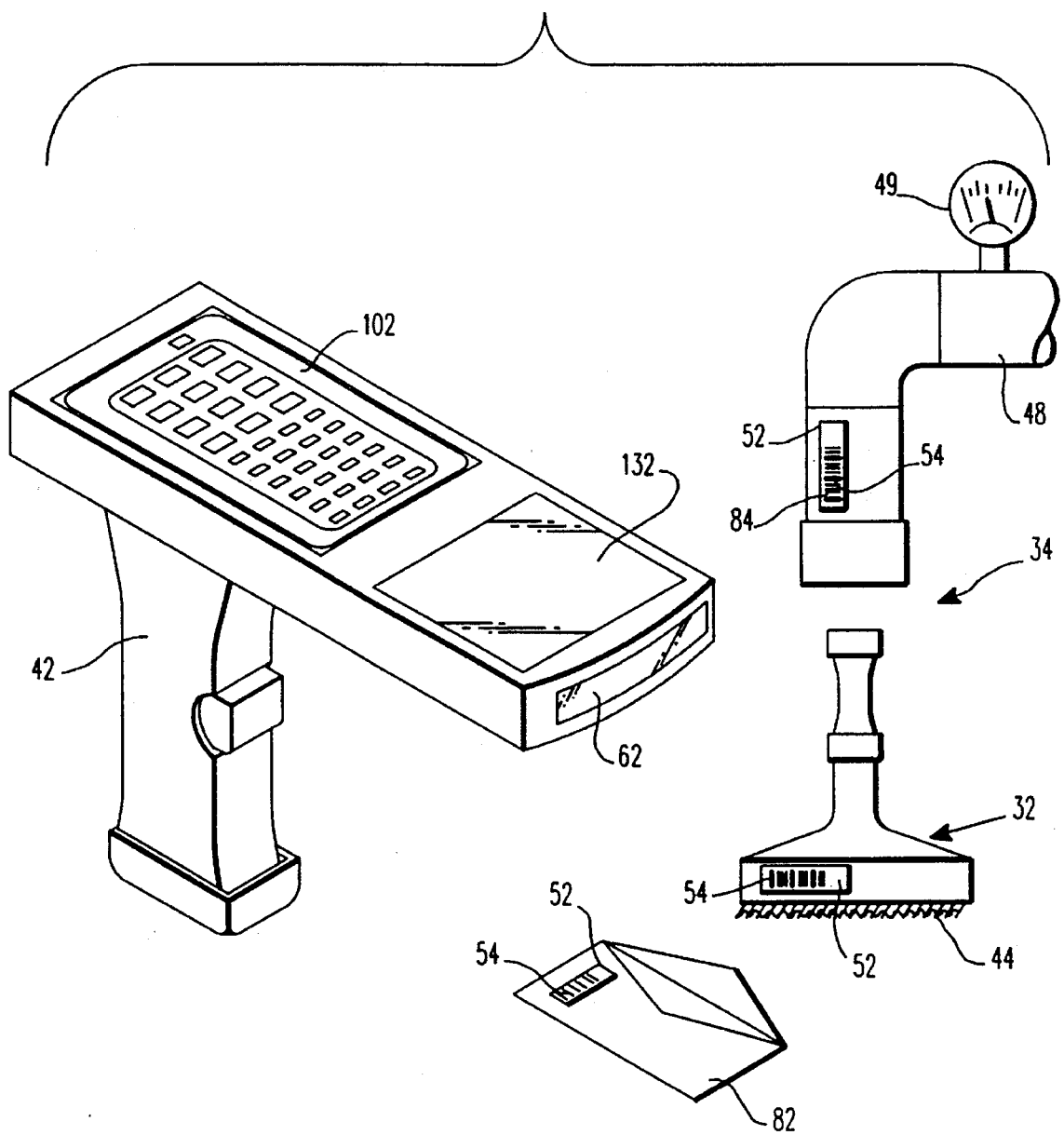
FIG. 2 is a partial perspective view illustrating a sample collection site, sample collector and portable data entry unit.

Referring to FIGS. 1 and 2, a monitoring system 22 is used in connection with sample collectors 32 for sensing an environmental parameter at a plurality of collection sites 34 by means of one or more portable data input devices 42. The sample collectors 32 can comprise, for example, filters 44 which can be mounted at the inlet of a suction line 48, by which ambient air at the collection site 34 is drawn through the filter 44, airborne dust being captured in the filter over time. Alternatively, the sample collector 32 can take a different form, such as a charcoal-type collector or silver zeolite collector, used to accumulate chemical species produced by nuclear decays, accumulated, trapped or adsorbed in the collectors 32.

The sample collectors 32 can be deployed, for example, at distributed collection sites 34 in a nuclear power plant, fuel or weapons handling plant or the like. In such a situation it is important to monitor radiation levels for protecting worker health and for enabling prompt response to equipment problems. For quick, convenient and accurate data collection according to the invention, each of the sample collectors 32 is associated with an automatically readable labelling means 52 representing an identity code 54 that uniquely distinguishes at least a subset of the sample collectors 32 from other sample collectors. Preferably, each sample collector is uniquely identified by its automatically readable identity code. When this identity code is read, time and date information are recorded simultaneously and automatically, permitting accurate and convenient entry of the deployment and collection times for each sample collector 32, and the monitoring of the locations of the samples over time.

The sample collectors 32 can be operable to capture a sample of a material such as a radioactive isotope that is the source of an environmental danger, namely radiation. Alternatively, the sample collectors can simply reflect an effect of the environmental parameter over time, such as by physical damage to the sample collector 32 resulting from radiation. In either case, the sample collector 32 can be tested or examined after exposure to the environmental parameter to determine the extent of change to the sample caused by a concentration of the environmental parameter in the area of the collection site. This extent of change to the sample varies as a function of the level of the environmental parameter, and also as a function of the time of exposure of the sample collector 32. Therefore it is necessary to factor the time of exposure into consideration when assessing the level of the environmental parameter during exposure of the sample.

In a preferred embodiment of the invention as shown schematically in FIG. 2, the sample collector includes a filter arranged at the inlet to a suction source. Whereas the amount of suction affects the quantity of air passing the filter, the amount of suction is a collection parameter that is pertinent to assessing the ambient concentration of dust collected on the filter. The pressure drop across the filter can be determined and recorded in the portable data entry unit as well, and indexed to the sample identity and to the collection site. For example, the pressure drop upon deployment and upon collection can be recorded, and the volume of air passing the filter can be estimated. Alternatively, a flow meter can be coupled along the suction line to determine the flow rate through the filter upon deployment and upon collection.

The time at the beginning of exposure (deployment of the sample collector) and the time at the end of exposure (recovery of the sample) are entered automatically by the processor in a portable data entry unit 42 when reading the identity code associated with at least one of the sample collector 32, the site 34 of deployment and the collected sample holding means 44. The "time" in this context is considered to include the date, in any situation in which the sample is to remain exposed for more than 24hours, i.e., to enable accurate calculation of the duration of exposure from the start (deployment) and stop (recovery and/or testing) times recorded. As discussed below, it is also possible to automate the collection of pertinent parameters at the collection site affecting flow through the filter.

In the case of collection of nuclear isotopes, it is necessary in assessing the level of radiation at the collection site not only to factor in the duration of exposure. The time delay between collection of the isotopes and analysis of the sample for emitted radiation must also be considered because nuclear decay of the collected isotopes over time reduces the present decay activity of the isotopes remaining in the sample. For some isotopes, the half life is so long that it can be ignored. Other isotopes may have a half life that is short enough to affect the calculations needed to assess the concentration of the isotope over the period of exposure. The time of day (or other time reference) is advantageously recorded upon deployment, recovery and testing of the sample. According to the invention this time data collection is done automatically upon scanning of the code 54 identifying the sample 44, the sample collector 32 and/or the sample collection site 34.

A portable data entry unit 42 is provided for use by the technician deploying the sample collectors 32 and recovering the samples. The portable data entry unit 42 includes means for reading the identity code 54. The identity code is preferably printed as a bar code on a label 52. A scanner or similar optical reader 62 illuminates the code 54, e.g., with a scanning beam directed perpendicularly across the spaced wide and narrow bar code bands, and detects the codes by sensing the corresponding changes in reflectivity.

Alternatively, the image of the bar coded label can be grabbed and recorded in a video memory for analysis by a processor 74 in the portable unit. In that case, the portable data entry unit is aimed at the code and triggered, whereupon an image of the code is recorded. The portable data entry unit can have a charge coupled device array operable to accumulate charge in individual pixel elements in an X-Y array. Suitable clocking and analog-to-digital conversion means digitize the charge level, and thus the incident light, for each pixel on which the image is focused, forming a pixel image of a single image frame. The processor then analyzes the pixel image for areas of contrast, which are decoded as wide and narrow contrasting bar code bands. This form of data reader is not limited to bar codes, but can also be used to obtain a single frame image of other pertinent features. For example, the reader can record an image of the face of a pressure or flow meter 49 coupled to the suction line as shown in FIG. 2, or even can record an image of the sample itself. In the event the image of a meter having a movable indicator line is recorded, the processor can determine the position of the indicator line automatically, can verify a reading entered by the operator, or simply record the image for future display. If the image is numerical, such as an odometer-style meter, LED or LCD display, the image data can be processed by optical character recognition algorithms encoded in the portable data entry unit.

Various forms of bar code and various forms of hand-held bar code readers are known. An appropriate form of bar code is the 3-of-9 bar code, although other forms are also possible. The identity code may include a number such as a serial number, or a combination of a serial number and certain numeric digits or alphanumeric characters that describe the type of sample, sample collector or collection site. The identity codes uniquely identify at least a subset of the sample collectors, samples and/or sites (e.g., those having aspects in common), and preferably uniquely identify each individual one.

Preferably, the portable data entry unit stores at least some information defining a profile of expected data from the site. For example, the site code can be indexed to maximum and minimum suction or air flow rate data for the site. In the event the operator enters a suction or rate value out of the maximum and minimum limits, the portable data entry unit can prompt the operator to reenter the data or to take appropriate remedial action, such as clearing the suction line, starting the vacuum pump coupled thereto, etc.

There are two preferred forms of optical readers employed in portable data entry units 42 according to the invention. One form uses a laser scanner to illuminate the bar codes and the other records a pixel image of the bar code label. Each of these forms provides an average signal which is useful for reading the codes, the scanner by using multiple scan passes and the pixel image by averaging the luminance of the bar code label over an acquisition time during which light sensitive elements are exposed to the image and enabled.

In a laser scanning unit the portable data unit is housed in a pistol grip casing enabling the unit to be pointed easily at the bar code label 52 such that the laser scanning line passes perpendicularly over the wide and narrow bars of the code. A photodetector responsive to the reflections of the bar code develops a signal that by appropriate known circuitry converts the signal to a numeric or alphanumeric code. A wand type scanner is possible, whereby the user strokes a light source and photodetector head over the bar code. However, a laser scanning device (e.g., having a rotating mirror for repetitively scanning over the code) is preferred in that an average signal can be developed. The scanning type reader thus has a much better ability to read lower quality bar code labels.

Figure 4:
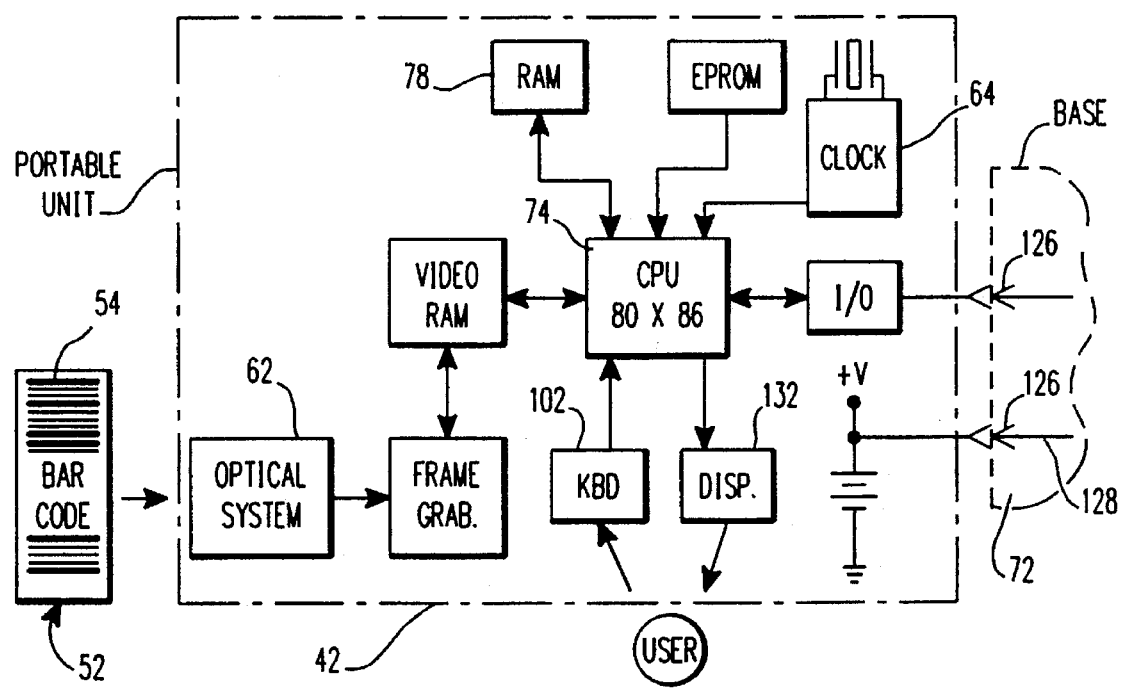

A preferred form of optical image reader is shown in block diagram form in FIG. 4. Instead of using a scanning laser, the image of the bar code label is recorded using an optical system and frame grabber comprising, for example, a charge coupled array sensor on which the image is focused. An analog to digital converter and timing means are coupled to the sensor array for digitizing the levels of charges developed in elements of the sensor array. An image is collected when the user operates a trigger or similar switch means on the optical reader. The digitized output of the sensor elements in the array are stored as a series of pixels in a video RAM coupled to the processor 74, for example an 80X86 central processor. The processor determines the code by analyzing the pixel data for variations in collected light level representing bar code bands.

The optical image reader is advantageous in that its input is not limited to recording bar code images. Although bar code images are a preferred manner of using the optical reader, this same form of optical reader can also record the image of other items, such as analog meter faces, from which data can be entered automatically via image analysis software. In connection with an analog meter, for example, the processor can search the image to locate reference markings on the meter face; align and subtract the stored image of the meter face (but for the indicator thereon); and determine the position of the indicator or other pointer which shows the value being read by the meter. It is also possible using this form of input device to record images which are not processed except for storage to enable the image to be examined later, e.g., the image of a filter element being collected.

The portable data entry unit 42 preferably includes a digital time clock 64 operable to provide a time at which the identity code 54 is read. Alternatively, the portable data entry unit 42 can be arranged to communicate with a remote processor, for example at a base station 72, which includes the time of day clock. In the embodiment shown, the portable data entry unit is a self contained device which collects codes, times and other information for uploading to the remote processor. However, the portable data unit can also be arranged simply to read codes, and to upload the codes over a communication path substantially contemporaneously with collection of the codes, in which case the time and code data is also made available for analysis. Such communications are typically by radio.

Preferably, the portable data entry unit 42 includes an on board processor 74 having the clock circuit 64 and coupled to an on board digital memory 78. The clock circuit can take several possible forms. For example, the processor can be programmed to maintain a count of the time of day and date as a programmed function triggered by periodic interrupts from clock circuit 64. Alternatively, the portable data entry unit 42 can be provided with a counter coupled to the clock oscillator circuit, from which the processor 74 can read the current time of day, and preferably date. Each time the optical reader 62 reads a bar code 54, the bar code data and the time of day are stored and indexed together in data memory.

Although the invention is described with reference to bar code reading, it will be appreciated that other forms of optical and electromagnetic encoding are also possible and can be used according to the invention. For example, and without limitation, other character recognition systems can be employed, such as OCR characters. Electromagnetic encoding such as passive RF encoding labels can be used as well. In each case the samples, sample collectors and/or sites are identified in a manner that facilitates automatic reading.

The technician servicing the environmental sampling system normally proceeds along a route, visiting each of the sample collection sites 34 along the route, one after another. The technician recovers the exposed sample collector 32 at each respective site 34 or extracts its sample, and replaces the sample collector at each site with a fresh one. For example, the technician removes the exposed air filter 44 from a sample collector 32 of the type coupled to a suction supply 48 as shown in FIG. 2. The air filter 44 may be encoded by a label, preferably bar coded, or alternatively is stored in a bar code labelled container such as envelope 82. In any event the technician scans or otherwise reads the bar code 54 identifying the sample, and preferably reads an additional bar code 84 which identifies the collection site 34. A fresh filter 44 is then placed in the sample collector 32.

The portable data collector preferably prompts the technician to enter additional data required to analyze the sample. Among other parameters, the flow rate of air through a filter element type collector is needed to assess the ambient concentration in the air being filtered. Normally, the flow rate is determined from a flow meter associated with the collection site or from the differential pressure across the filter, one or both of these being represented in the drawing by meter 49. Additional parameters such as temperature, humidity, barometric pressure and the like may be necessary or useful for assessment of the concentration of the conditions being monitored. For example, the absolute pressure in the suction line as well as the barometric pressure could be entered to determine filter back pressure. Together with the flow rate (which when integrated over time represents the volume of air passing the filter), this information can be collected when deploying the filter and again when collecting it, and used to assess or estimate such factors as the amount of air borne dust collected by the filter or the concentration of dust in the air, in addition to ambient radiation level. A variety of test procedures are facilitated in this manner.

After completing the route, the codes represented by the bar codes 54 have been stored in memory, and indexed to the time of day at which the codes were input by the optical reader. This information is matched to the information respecting deployment of the samples which was stored previously, namely when the fresh filter 44 was initially deployed.

After completing the route, the portable data entry unit 42 is coupled in data communication with the base processing unit 72. The base processing unit also has a processor 92 and data memory 94. The base processing unit is operable to store at least the identity codes and times for each of the labels read by the portable data entry unit.

Normally, the deployment times of particular sample collectors are recorded during a first cycle of servicing using the portable data entry unit, and the recovery times of the samples are recorded during some later cycle. Therefore the deployment time indexed to a particular sample identity code may be stored in the memory of the base processor 72 for a while, waiting to be matched with a recovery time of the particular sample. Alternatively, the portable data unit 42 can be programmed to store the deployment times and identity codes until sample exposure is complete, and to transfer to the base processor the records for only those samples which have been recovered.

Preferably the sample identity codes and deployment times are stored in the base processor 72. In this way it is not necessary that the same portable data unit 42 be used when recovering a sample as when deploying the sample. Variations on the programming of the portable data entry unit 42 and the base processor 72 are possible. For example, matching deployment and collection times with the corresponding identity code can alternatively be accomplished by either of the portable data collection units and the base processor.

As shown in FIG. 2, the portable data entry unit 42 preferably includes a keypad 102 for entering numeric and/or alphanumeric data as well as switches for operating the optical reader 62, such as a trigger to effect capture of an image of the encoded label 52. The keypad 102 can be used for entering various information relating to the monitoring system. For example, the technician preferably enters his or her name or a personal identity code at least when beginning a deployment/recovery operation. The processor 74 in the portable data unit 42 can prompt the technician to enter this data, as well as data respecting factors such as the type of sample collection site being visited, parameters measured at the collection site such as flow rate through a filter, etc.

The software procedures in the portable data unit 42 can include profile information relating to the sites 34 or to categories of the sites, such as the equipment configuration expected at the site. When the site code is read or if the portable unit 42 is arranged to require entry of data via the keyboard 102 to describe the site, the processor 74 can compare this information to the stored profiles and reject data that does not fall into expected ranges. For example, if the software expects a certain type of site 34 to have a particular type of sample collector 32, it can alert the technician to an error if reading the associated code shows that an unexpected sample collector 32 has been used. If the stored profile respecting a collection site is such that a certain data value is illegal for the site, the technician can be alerted immediately and can take appropriate remedial action. Re-entry of the data or other corrections can then be effected.

Having collected at the base unit 22 the respective times of deployment and recovery of the samples, as indexed to the sample identity codes and cross referenced to the respective sites, as well as any necessary information respecting the manner in which the sample was collected (e.g., air flow rate), the samples are then analyzed to determine the level of exposure of the sample to the radiation or to another environmental parameter. The test data can be collected using a separate testing means 104 coupleable to the base processing unit 92 for transferring the results of tests on the samples to the base processing unit. This test data is also indexed to the sample code. Preferably, the testing means for assessing exposure of individual samples to the environmental parameter operates in conjunction with the base processing unit for storing in the data memory 94 of the base processing unit a numerical assessment of exposure.

For this purpose, the testing means 104 and an additional optical reader or scanner 112 are coupled to the base processor 92. For testing the samples, the respective sample code 54 is read from the sample, or preferably from the envelope 82 containing the sample, using the additional scanning device 112. The sample is loaded into the testing means 104 and analyzed, the results being reported by the testing means 104 to the base processor 92 in conjunction with the identifying code 54 read by the scanner 112. The base processor 92 indexes the results of the testing to the sample identity code 54, and preferably to the site 34 at which the sample was exposed.

In connection with testing for the emissions of radioactive isotopes, the time between recovery of the sample and testing is needed to obtain an accurate representation of the level of the environmental parameter, to account for isotopes having a half life which is relatively short. The testing means 104 typically includes a detector responsive to alpha particles (i.e., helium nuclei consisting of two protons and two neutrons) and/or beta particles (i.e., an electron or positron) emitted from the sample as products of nuclear decay. The testing means can have a semiconductor detector element, a scintillation detector or another element which produces pulses upon impingement of a nuclear particle. These pulses are counted over a predetermined period of time to assess the amount of the isotope present in the sample.

The base processor 92 is programmed to normalize the apparent amount of the isotope or chemical species in the sample using the delay between recovery of the sample and testing. The processor also normalizes the results to apply the apparent amount of isotope or chemical to the volume of air passing the filter (assuming a filter type collector), as determined from flow rate information collected by the technician upon deployment and upon recovery of the sample collector. Furthermore, the processor accounts for the time of exposure (i.e., a portion of the isotope collected earlier may have decayed during the time of exposure as well as between recovery and testing) as well as for other variables in the process which can be determined partly from data entered by the technician and partly due to the automatic time recordation function of the portable data entry unit.

At least one report of the exposure can be generated by the base processor 92 for each of the plurality of sample collectors 32, or for a selected group of sample collectors. There are various ways in which the data can be reported. In connection with a single cycle of sampling and testing, the report can include, for example, an overall estimation of exposure, a spatial distribution of the levels of exposure at the distributed collection sites 34, alarm means if a detected level exceeds some threshold, and other such reports. In connection with a plurality of successive cycles of sampling and testing, the exposure level at one or more sites can be plotted over time. In connection with a plurality of successive samples from a given site, the data can be grouped to form a composite of the results for the site, e.g., all the samples for a given month from a particular site may provide a statistically more significant composite than individual samples exhibiting a high standard of deviation. A display means 114, printer 118, or similar output device is coupled to the base processor 92 to read out these and other similar reports.

A sample of a possible report is shown as Table I. In addition to information identifying the collection site and time, this report shows certain of the maximum/minimum parameters of the data profile applicable to the site, and the values of parameter values which are manually entered as part of the process and/or which are input via the image capture capability of the portable unit.

TABLE I

| Location Code: S289 | | | Type: Stack |
|---|---|---|---|
| Reporting Designator: 02111 | | | |
| Full Description: S-PLANT 222_S BUILDING EXH296-S-21 | | | |
| REC. SAM. (STACK RECORD) | | | |
| Abbreviated Description: 2ND LEVEL | | | WHITE ENV. |
| Mon Tue Wed Thu Fri Sat Sun | | | |
| Schedule | T | | Stack Flow: 63443 |
| Equipment Configuration: | | | |
| | Exist Units | Min Value | Max Value |
| Gasmeter: | T Cu M | 0.0 | 100000.0 |
| Timer: | T | 0.0 | 336.0 |
| Rotameter: | T Cu Ft/Min | 1.6 | 2.4 |
| Vacuum: | T In Hg | 2.0 | 10.0 |
| Upper Limit | Alpha: 6.0e-014 | Beta: 3.0e-011 | Label: DCG |
| Lower Limit | Alpha: 1.0e-010 | Beta: 1.0e-009 | Label: DAC |
| Location Status: ACTIVE | | | |

The identity codes 54 are preferably unique to the sample or site. It is also possible to provide identity codes which are not unique, but describe the site 34 or sample collector 32 in a meaningful way. For example several samples or sites may have an attribute in common, such as location in a particular room or comparable proximity to a potential source of radiation. It is normally advisable to track the samples individually such that the monitoring system can account for the status and history of each, using unique codes; however it is also conceivable that some other subset or subdivision of samples or sites could share an identity code and be processed as one unit.

Preferably, the identity code and the site code are provided in a similar form, in particular by bar coding. In this manner the portable data entry unit 42 is conveniently operable by the user to read the identity code and the site code. The user simply aims and triggers the data entry unit. Whereas the sample code and the site code become associated together in memory, it is only necessary to read the site code upon one of deployment of the sample collector 32 and recovery of the sample. Reading the site code at both of these times can be done to enable redundant checking.

In a typical application of the invention, sampling and testing is done regularly, using a sufficient number of collection sites to promptly detect a problem, and to reflect the extent of worker exposure to a statistically significant level. The number of sampling sites and the number of samples taken may be large enough to require several technicians servicing several different routes to visit all the sites. Each of the technicians is provided with a portable data entry unit 42. Insofar as the base processor 92 is provided for correlating the deployment times, recovery times and site identity with the sample identity codes, it is not necessary that the same portable data entry unit 42 be used both when deploying a given sample and recovering it. The portable data entry units 42 can simply log the code and time into memory, together with any additional data entered by the technician, for later transfer to the base processor 92. At the base processor, all the data applicable to a particular monitoring cycle and site can be brought together as indexed to the sample identity code. Once stored in the data processor, the information forms a database from which reports can be generated.

A data transfer station 122 is preferably provided and coupled to the base processor 92 as shown in FIGS. 1 and 4, for servicing a number of the portable data entry units 42. The transfer station 122 can include cradle means 124 for supporting the portable data entry units 42, including data connectors 126 such as telephone-type connectors, D-type serial port connectors or the like, which engage when the portable units 42 are plugged into the cradles 124. The transfer of data can be automatic when a portable unit 42 is plugged in, or can require initiation of data transfer by the technician or operator.

Figure 3:
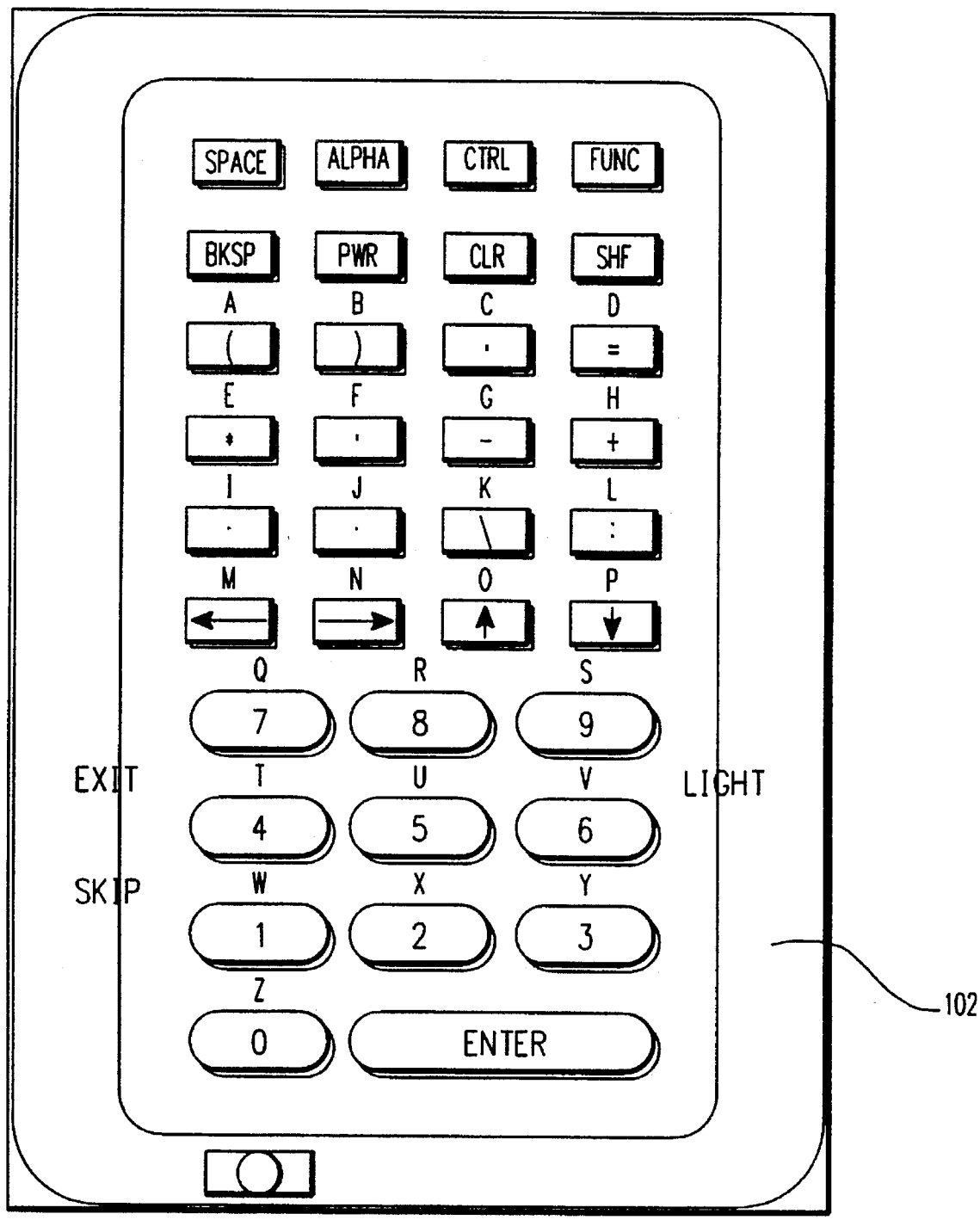
FIG. 3 is a plan view showing the keyboard of the portable data entry unit; and, FIG. 4 is a schematic block diagram showing the contents of the portable data entry unit.

The data transfer station 122 conveniently includes a power supply 128 which is coupled to charge the on-board batteries of the respective portable units 42 when they are plugged into the cradles 124. FIGS. 1–3 show the physical aspects of the portable data entry units, and FIG. 4 shows the electrical aspects. These units are primarily simply code readers having an automatic time entry means associated with the code reading process, and can comprise a simple CPU 74 or another form of controller for effecting these functions. Preferably, the processors 74 of the data entry units 42 also manage input and output with the user, e.g., accepting data from the keypad 102 and including at least a minimal display 132 and/or audio output for prompting the operator to take particular actions, for indicating successful reading or decoding of a sample code or site code, and the like. The processor can also include other functions for the convenience of the user or for improving data collection success and accuracy. For example, the processor can include a check on the reasonableness of data entered, by comparing the data to predetermined stored values.

The keypad 102 can be used as an alternative data entry means, for example for entering a site code manually in the event that the coded label cannot be read or decoded due to damage, dirt or the like. Optionally, the keypad can be used in conjunction with the processor 74 for reviewing the stored information, clearing old data, conducting diagnostic tests and the like. As shown in FIG. 3, the keypad includes not only numeric keys, but also function keys applicable to data entry and display. Certain of the keys provided for symbol entry or number entry can be alternatively operable to enter alphanumeric data, using a shift function.

Whether the identity code is entered by scanning or by use of the keypad, the code and the time are associated automatically. This information can also be stored and indexed against the sample codes and site codes, or against another code which is related to the sample code by a lookup table in memory. The information entered, including the data developed by testing means 104, enables the base processor to maintain a database of information on sampling. The data can be analyzed as to any of the variables maintained, including sample identity, time, location, exposure level, technician identity, time delay, type of sample or site, range of value for one or more of these variables, etc. A wide variety of reports which may be useful in particular circumstances are possible by selection, sorting, limiting, averaging and otherwise operating on the data as a function of the data collected both automatically and from user input.

An important benefit of the invention is the capability to determine at any time, or after the fact, the status and history of all the uniquely encoded sample collectors. It is thus possible not only to report the sample collector data and to analyze the data for patterns. It is furthermore possible, to report a chain of custody for the samples as a means for tracing problems or anomalous test results. A complete audit trail including times, places and identity codes are made available, ensuring regulatory compliance, and facilitating the management, collection and organization of a complete set of data with minimal effort.

The automated nature of the environmental testing method and apparatus according to the invention substantially improves accuracy of the test data, and also makes the data subject to more meaningful interpretation. For example, a technician can enter data including a variable representing the accuracy of a particular reading, e.g., the resolution of a meter as a percentage of full scale. Alternatively, the resolution of meters and the like can be determined from the stored profile data on a particular site. In any event, the accuracy of this initial data can be carried through calculations by the processor and duly reported. Propagation of an error figure in this manner provides a measure of the accuracy of data developed as a result of calculations on variables which each contribute to the error in the result.

The invention is applicable to various environmental parameters which can be sensed by their effects on samples over time, and is particularly applicable to the specific problems of detecting the level of exposure to nuclear radiation at distributed sites. The invention is not limited to this application, however, and is also applicable to the monitoring of other processes which involve a number of collection sites and/or samples to be monitored in a testing procedure. Some examples are chemical manufacturing processes such as refineries, other manufacturing processes, the reading of utility meters (e.g., water, electricity, gas, etc.), and to the general monitoring of environmental conditions for potential dangers.

The full automation advantages according to the preferred embodiment of the invention go beyond the capture and correlation of site identity, sample identity and temporal stamp. It may be desirable, or necessary to the calculations, to capture additional data from measuring equipment at the site as well, preferably as identified in the personality profile of the site stored in the portable data unit or perhaps communicated to the portable data unit over a communication path. For example, variables such as sampler flow rate, filter differential pressure (vacuum) and the like are suitably recorded. The values of these variables may be entered by operator input on keyboard 102, or via the image capture apparatus 62 and decoding algorithms operated by the portable unit (or by the base processor after uploading of image data from the portable unit. Such additional data are generally required to properly determine a final analyte air concentration value.

The use of the image capture apparatus 62 provides capability to evaluate automatically various type visual indicators. This feature is a substantial advantage in applying the invention to operations having mechanical or visual readouts which have not been automated due to considerations of cost and modernization schedules. Some examples include utility electrical and gasmeter readouts, process gauges and odometer-style integrating meters.

The apparatus as disclosed includes a significant capability for expansion. The base processor can be coupled in a network supporting several workstations. The workstations 92 include local processing of field unit data, initial communications support for the field unit through the docking station 122, and local report generation and data maintenance. The workstations, for example, can be networked to a file server containing a master data base. Full autonomous and concurrent support of the multiple workstations is supported. Variable user access levels can be arranged using a user authorization and access control arrangement, for example with users being generally permitted to view the data but not necessarily being authorized to change key system variables or elements affecting the reported results. A multi-user facility of this type can service a number of different locations, e.g., with communications over inter-user distances of many miles being accomplished via currently available data communications topologies.

The invention having been disclosed, variations will now be apparent to persons skilled in the art. The invention is not intended to be limited to the exemplary embodiments discussed in detail, but also to encompass a certain range of such variations. Accordingly, reference should be made to the appended claims rather than the foregoing discussion of examples, in order to assess the scope of the invention in which exclusive rights are claimed.

We claim:

1. A method for automatic monitoring of an environmental parameter at a plurality of collection sites, comprising the steps of:

deploying sample collectors at each of the collection sites, and uniquely distinguishing at least a subset of the sample collectors from other sample collectors by associating with the sample collectors an automatically readable means representing an identity code;

exposing the sample collectors at the collection sites to capture samples representing an effect of the environmental parameter at the collection sites;

collecting the samples, and automatically reading the identity codes upon at least one of said collecting and said deploying, using a portable data entry unit having means for reading the identity code and means for determining a time of said reading, and storing the time of the reading, indexed to the identity code;

communicating a plurality of said identity codes and times from the portable data entry unit to a base processing unit, and storing said identity codes and said times in a data memory coupled to the base processing unit;

testing the samples for assessing exposure of individual said samples to the environmental parameter, and storing in the data memory a numerical assessment of said exposure, indexed to the respective collection site;

generating at least one report of said exposure for each of the plurality of sample collectors; and uniquely distinguishing the collection sites by a site code fixed thereto, and wherein the identity code and the site code are optically read by an image grabber coupled to the portable data entry unit, the site code being read at least once during deployment of the sample collector and collection of the sample, for associating the sample with a particular site.

2. The method for automatic monitoring according to claim 1, further comprising entering via the portable data entry unit at least one site data parameter value affecting the numerical assessment, the site data parameter value being entered by at least one of manual keyboard entry and optical reading of an indicator at the site representing the site data parameter value.

3. The method of claim 1, wherein the optically read identity code and the site code include a bar code.

* * * * *